US00PP13517P2

(12) United States Plant Patent
Lemon

(10) Patent No.: US PP13,517 P2
(45) Date of Patent: Jan. 28, 2003

(54) GERANIUM PLANT NAMED 'ROYALTY WHITE'

(75) Inventor: David Lemon, Santa Barbara County, CA (US)

(73) Assignee: Olgevee, Ltd., Connellsville, PA (US)

( * ) Notice: Subject to any disclaimer, the term of this patent is extended or adjusted under 35 U.S.C. 154(b) by 0 days.

(21) Appl. No.: 09/877,149

(22) Filed: Jun. 8, 2001

(51) Int. Cl.[7] ..... A01H 5/00
(52) U.S. Cl. ..... Plt./331
(58) Field of Search ..... Plt./331

*Primary Examiner*—Bruce R. Campell
*Assistant Examiner*—Annette Para
(74) *Attorney, Agent, or Firm*—Webb Ziesenheim Logsdon Orkin & Hanson, P.C.

(57) ABSTRACT

A new and distinct regal geranium plant with large lacy white colored flowers having orchid colored eyes forming full flower heads and above medium green foliage.

1 Drawing Sheet

CLASSIFICATION

*Pelargonium×domesticum.*

VARIETAL DENOMINATION

'Royalty White'.

BACKGROUND OF THE INVENTION

The present invention comprises a new and distinct cultivar of *Pelargonium×domesticum* known by the varietal name 'Royalty White', Breeder No. 5DG1941. The new variety was discovered in Lompoc, Calif. The new variety is a result of cross breeding of White Champion (female) (unpatented) and Duchess (male) (U.S. Plant No. 8,074). The new variety exhibits similar flower color to White Champion and similar habit to Duchess, but differs in its early flowering compared to White Champion and improved flower type over Duchess. The new variety was first asexually reproduced by cuttings in Connellsville, Pa. The new variety has been trial and field tested and has been found to retain its distinctive characteristics and remain true to type through successive propagations.

The new variety, when grown in a glass greenhouse in Connellsville, Pa. using full light, 60° F. night temperature and 68° F. day temperature and grown in a soilless media with constant fertilizer at 200–250 ppm nitrogen and potassium has a response time of 13 weeks to flowering from a rooted cutting to flowering in a 6 inch pot.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar at 10 weeks grown from a rooted cutting. The data which defines these characteristics were collected by asexual reproductions carried out at Oglevee, Ltd. in Connellsville, Pa. The color readings were taken from a plant grown in a glass greenhouse. Color references are primarily to The R.H.S. Colour Chart of The Royal Horticultural Society of London.

PLANT

Form: Medium mound.
Height from media surface: 15–17 inches from soil to top of foliage.
Growth: Upright, free basal branching.
Strength: Does not require artificial support.
Foliage: Stalked leaf arrangement.
Leaves:
- *Size.*—7–9 cm long; 10–12 cm wide.
- *Shape.*—Reniform; truncate base.
- *Margin.*—Serrated; slightly lobed.
- *Texture.*—Leathery, pubescent.
- *Color.*—Upper surface: Green Group 137C. Lower surface: Green Group 138B.
- *Ribs and veins.*—Type: Palmate. Color: Yellow-Green Group 145C.

Petioles:
- *Color.*—Yellow-Green Group 144A.
- *Length.*—6–9 cm.

Stem:
- *Color.*—Yellow-Green Group 144A.
- *Internode length.*—2–4 cm.

THE BUD

Shape when just showing color:
- *Overall.*—Elliptical cluster.
- *Individual bud.*—Ellipitcal.

Size when just showing color:
- *Size of cluster.*—3.5–4 cm wide.
- *Individual bud.*—1.5–2 cm long.
- *Number of buds per cluster.*—5–7.

INFLORESCENCE

Blooming habit: Continuous; large florets forming full flower heads.
Size of umbel: 7–9 cm wide.
Borne: Flowers on umbel; umbel on pedicel; pedicel on peduncle.
Number of flowers per umbel: 6–9.

Flowers:

*Form.*—Cupped; ruffled edges.

*Size.*—4 cm across; 3–3.5 cm deep.

*Petals.*—Shape: Obovate. Size: 3–3.5 cm wide; 4 cm long. Margin: Entire. Number per flower: 5. Color: Upper surface: White Group 155D. Lower surface: White Group 155D with eye showing through. Eye: Outer edge is Red-Purple Group 71D moving to a darker purple, Red-Purple Group 72A. Veining ranges in color from Red-Purple Group 71C to Purple Group 77 fading to pale lavender color at base of petal, Red-Purple Group 70D.

*Texture.*—Smooth, velvety.

*Tonality from a distance.*—White florets with orchid eye and veining.

Petaloids: None observed.

Pedicel:

*Length.*—1.5–2 cm.

*Color.*—Yellow-Green Group 144A.

Peduncle:

*Length.*—4.5–5.5 cm.

*Color.*—Yellow-Green Group 144A.

Disease/pest resistance: No unusual susceptibility to diseases or pests has been noted to date.

Lasting quality: Individual umbels will last in the home environment for 4–6 weeks; overall flowering will continue as long as conditions remain cool at night with plenty of light provided.

Fragrance: None.

REPRODUCTIVE ORGANS

Stamens:

*Quantity.*—7.

*Anthers.*—4–5 mm long.

*Filaments.*—Length: 1.5–1.8 cm. Color: White.

*Pollen color.*—Golden brown.

Pistils:

*Number.*—One.

*Length.*—1.7–2 cm.

*Stigma.*—Number: One; parted. Color: Purple.

*Style.*—Length: 1–1.2 cm. Color: Greyed-Purple Group 187C.

Ovaries:

*Color.*—Green.

*Length.*—6–7 mm.

*Width.*—3 mm.

*Pubescence.*—Greatly pubescent.

*Completeness.*—Superior.

Fruit: None observed.

GENERAL CHARACTERISTICS

This plant is characterized by a tall mound of green foliage which is topped by an abundance of white lacy florets. The lacy white effect is enhanced by a striking orchid eye and veining.

I claim:

1. A new and distinct variety of regal geranium plant substantially as shown and described.

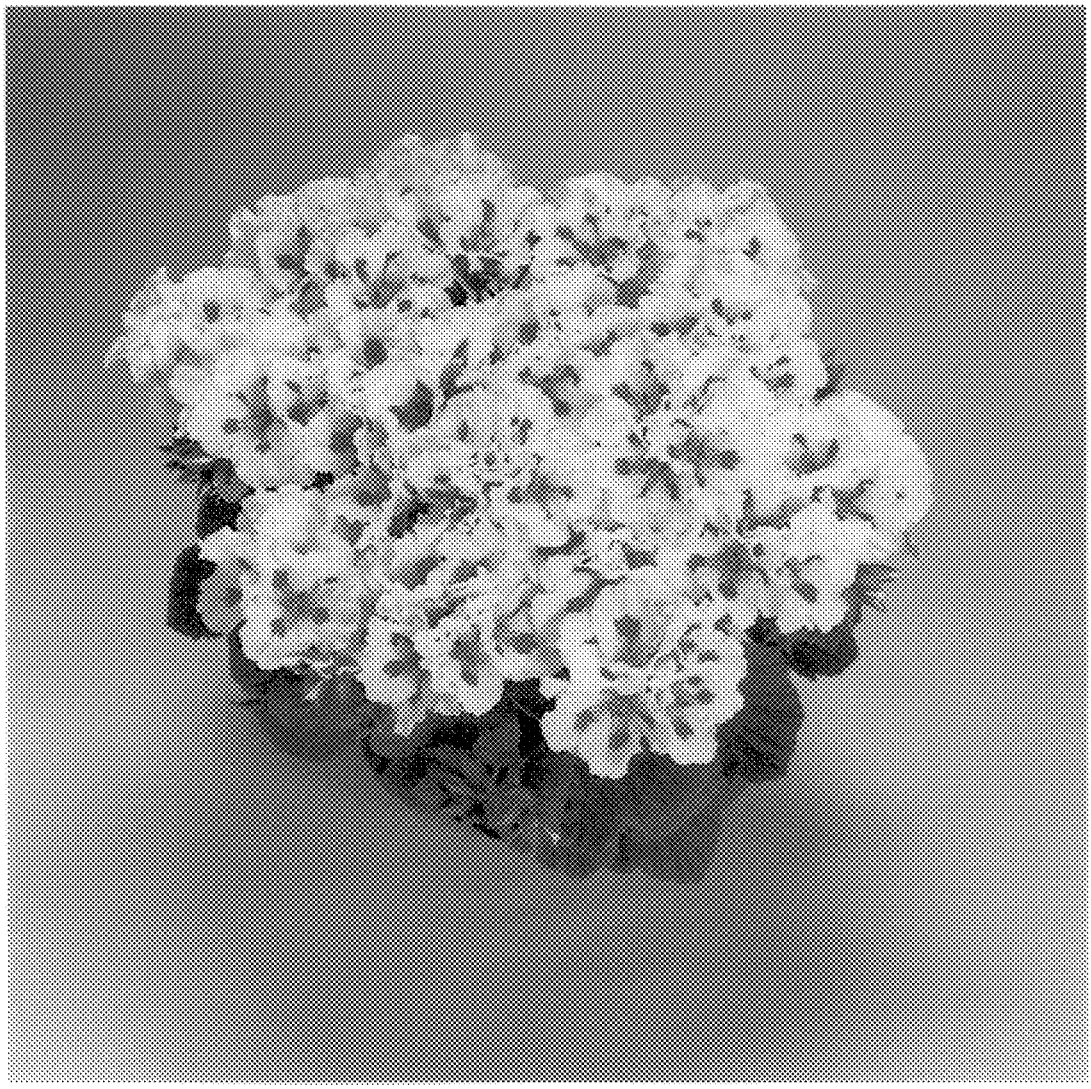

* * * * *